US011800851B2

(12) United States Patent
 Coyle

(10) Patent No.: US 11,800,851 B2
(45) Date of Patent: Oct. 31, 2023

(54) LIGHT CAPSULE

(71) Applicant: Brian Michael Coyle, Canyon, CA (US)

(72) Inventor: Brian Michael Coyle, Canyon, CA (US)

( * ) Notice: Subject to any disclaimer, the term of this patent is extended or adjusted under 35 U.S.C. 154(b) by 453 days.

(21) Appl. No.: 16/729,399

(22) Filed: Dec. 29, 2019

(65) Prior Publication Data

US 2021/0196972 A1    Jul. 1, 2021

(51) Int. Cl.
| | |
|---|---|
| *A61N 5/06* | (2006.01) |
| *A01K 11/00* | (2006.01) |
| *F21V 15/01* | (2006.01) |
| *F21V 23/02* | (2006.01) |
| *F21V 29/70* | (2015.01) |
| *F21V 23/04* | (2006.01) |
| *A61D 99/00* | (2006.01) |

(52) U.S. Cl.
CPC ............ *A01K 11/007* (2013.01); *F21V 15/01* (2013.01); *F21V 23/02* (2013.01); *F21V 23/0435* (2013.01); *F21V 23/0442* (2013.01); *F21V 29/70* (2015.01); *A61D 99/00* (2013.01); *A61N 5/0603* (2013.01); *A61N 5/0624* (2013.01); *A61N 2005/0609* (2013.01); *A61N 2005/0626* (2013.01); *A61N 2005/0663* (2013.01)

(58) Field of Classification Search
CPC .. A61N 5/0624; A61N 5/0601; A61N 5/0603; A61N 2005/0609; A61K 9/0068
See application file for complete search history.

(56) References Cited

U.S. PATENT DOCUMENTS

| | | | |
|---|---|---|---|
| 4,637,816 A * | 1/1987 | Mann ..................... | A61D 7/00 604/77 |
| 4,992,768 A | 2/1991 | Mozis et al. | |
| 7,289,011 B2 | 9/2007 | Tan | |
| 10,306,868 B2 | 6/2019 | Rettedal et al. | |
| 10,390,515 B2 | 8/2019 | Bancroft et al. | |
| 2001/0049464 A1* | 12/2001 | Ganz ..................... | H01J 35/32 600/3 |
| 2012/0226335 A1* | 9/2012 | Surrenti ............... | A61N 5/0603 607/92 |

(Continued)

FOREIGN PATENT DOCUMENTS

KR          100998722 B1 * 12/2010  ............... A61N 5/06

OTHER PUBLICATIONS

Irwin, D.M., Evolution of the bovine lysozyme gene family. changes in gene expression and reverse of function, Journal of Molecular Evolution, 1994(41). 299.

(Continued)

*Primary Examiner* — Allen Porter
*Assistant Examiner* — Skylar Lindsey Christianson

(57) ABSTRACT

The present invention relates to methods, systems, and devices that emit light energy in the ruminant rumenoreticulum, to inactivate a quantity of microbes. The device is a size or shape that will obtain a predetermined position within the rumenoreticulum, and protectively contains long lasting battery power, electric components, and light sources that emit wavelengths that inactivate and destroy microbes. The device, the system and the method according to the present invention also allow detection of biological parameters of the capsule environment and communication with a receiver outside the animal.

18 Claims, 9 Drawing Sheets

(56) References Cited

U.S. PATENT DOCUMENTS

| | | | |
|---|---|---|---|
| 2014/0005758 A1* | 1/2014 | Ben-Yehuda | A61N 5/0603 607/92 |
| 2019/0134419 A1* | 5/2019 | Bourke, Jr. | A61P 37/06 |
| 2021/0128933 A1* | 5/2021 | Sa | A61N 5/0603 |

OTHER PUBLICATIONS

Huntgate, R.E., The Rumen Microbial Ecosystem, Annual Review of Ecology and Systematics, 1975(6): 39-66.

Lobritz, M.A., Belenky, P., Porter, C.P.B., Gutierrez, A., Yang, J.H., Schwarz, E.G., Dwyer, D.J., Khalil, A.S., Collins, J.J., Antibiotics and bacterial respiration, Proceedings of the National Academy of Sciences, Jul. 2015, 112(27): 8173-8180.

Russell, J.B., and Rychlik J.L., Factors That Alter Rumen Microbial Ecology, Science, May 11, 2001, (292)5519: 1119-1122.

Leggett, H.C., Cornwallis, C.K., West, S.A., Mechanisms of Pathogenesis, Infective Dose and Virulence in Human Parasites, PLoS Pathogens, 2012, 8(2): e1002512.

Gama, J.A., Abby, S.S., Vieira-Silva, S., Dionisio, F., Rocha, E.P.C., Immune Subversion and Quorum-Sensing Shape the Variation in Infectious Dose among Bacterial Pathogens, PLOS/Pathogens, 2012, 8(2): Supplemental Material.

Monteagudo-Chu, M.O., Shaeishaa, N., Duration of Antibiotic Therapy: General Principles, pharmacytimes.com, publications/health-system-edition/2017/July2017/duration-of-antibiotic-therapy-general-principles.

MacLean, M., MacGregor, S.J., Anderson, J.G., Wools, G., Inactivation of Bacterial Pathogens following Exposure to Light from a 405-Nanometer Light-Emitting Diode Array, Applied and Environmental Microbiology, 2009, 75(7): 1932-1937.

Atreya, C., Glynn S., Busch, M., Kleinman, S., Snyder, E., Rutter, S., Aubuchon, J., Flegel, W., Reeve, D., Devine, D., Cohn, C., Proceedings of the Food and Drug Administration public workshop on pathogen reduction technologies for blood safety, Transfusion, 2018, (59)9: Conference Report: 1-33.

* cited by examiner

LIGHT CAPSULE

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

I. Field of the Invention

This invention relates generally to an encapsulated luminaire designed to be deposited in a stomach of a ruminant animal, such as a cow, for inactivating some of the microbes in the animal's digestive system. More particularly, the invention pertains to a method of promoting animal growth and health that can substitute for the use of sub-therapeutic dosages of antibiotics, without inducing antimicrobial resistance, which has become a public health crisis. Also, the invention pertains to a method of decreasing methane production in the animal's digestive system.

II. Discussion of the Prior Art

The ruminant digestive system exploits microbes. Vast numbers (hundreds of trillions) of fermentative microbes flow into their stomachs. These microbes digest foodstuffs and are themselves a major source of protein and methane. Ruminants are not like other animals, such as humans, whose digestive systems get rid of microbes in feces. Instead many ruminant microbes are "deconstructed" in the abomasum, one of their stomachs. The abomasum secretes large amounts of lysozymes, enzymes that hydrolyze the glycosidic bonds in microbe cell wall mucopolysaccharides. Once ruptured, the bacterium's internal material is consumed by other microbes, or absorbed by the animal. Microbe residues make up a significant part of a ruminant's protein source (Irwin, D. M., 1995, 1.)

This dual use of microbes by ruminants establishes a competitive equilibrium. Higher microbe levels can lead to higher levels of protein consumption, and increased fermentation can lead to more carbohydrate and energy consumption. But microbes also compete with the animal for food, and too many reduce the ruminant's consumption level. Too many microbes also cause excess fermentation and trigger immune system activity. Killing some microbes with interventions like antibiotics can avoid these problems, while making available microbial proteins.

When the ruminant eats, particles flow down the esophagus and into the rumen, where they flow freely between the rumen and reticulum, hence the term rumenoreticulum. This area contains about half the digestive capacity, in a full grown cow perhaps 40 liters of an 80 liter digestive capacity. It contains the majority of microbial activity. The rumen contracts severely to mix its contents. Most animals cannot digest cellulose. Ruminants delegate the process to microbes. Microbes digest cellulose to produce their own energy, and release volatile fatty acids (VFAs) that provide 70% of the cow or steer's energy supply (Hungate, 1975, 2.) Microbes also produce prodigious amounts of $CO_2$ and methane, which cattle belch (contributing 3% to 5% of global warming.)

The problems of digesting grains, primarily corn, as used in feedlots, illustrates the difficulty of maintaining a competitive equilibrium in ruminant microbial digestion. Corn is more rapidly fermented than roughage by microbes. Grains produce more VFAs, especially Proprionic acid. They also produce more gasses. The animal reduces stomach contractions, because material is more easily mixed. More gas, but less movement to belch it, can lead to "bloat" or even asphyxiation. Bacteriostatic antibiotics, which reduce microbial respiration, can reduce fermentation rates. Accelerated fermentation also leads to more acidic conditions. This pH change promotes pathogenic microbe growth, with serious downstream effects like liver failure. Antibiotics counteract such illness (Lobritz, M. A., et al., 2015, 3.)

Feedlots exhibit, in exaggerated form, the general dilemma of ruminant microbes. Farmers want to promote digestive microbe activity, which leads to increased growth. But higher levels of activity distort the ruminant's digestive system, including reduced animal uptake of nutrients and excess production of gasses and acids, which impact ruminant health and undermine growth. Sub-therapeutic dosages of antibiotics (STAs) destroy some microbes, which allows the ruminant to digest microbial contents while avoiding excess microbial activity (Russell & Rychlik, 2001, 4.)

The use of STAs are widespread in cattle in the US and globally, and are considered a major promoter of antibiotic resistance (AMR.) Resistant microbes enter the environment through urine, manure, particulates, in stalls and feed lots and manure applications. Humans may be exposed through environmental contact, animal-human contact, through consuming residues in meat and by-products. Microbes in human environments exchange genes with microbes further away, including agriculturally sourced AMR genes. STA bans exist in Europe, and are proposed elsewhere, but there is no substitute product that can duplicate their effect. In many developing countries antibiotics are largely unregulated, and STA usage may pass AMR swiftly into the human food chain.

When antibiotics kill microbes, the cell membrane disintegrates, a process called lysis. The microbe cytoplasm, robosomes, and proteins are exposed. Other microbes consume them, or they are absorbed in digestion. Farmers need an alternative way to lyse an amount of ruminant microbes similar to the amount killed by antibiotics, to help avoid AMR.

STA dosages only inactivate a small fraction of ruminant rumenoreticulum microbes. To estimate this, consider the concentration of microbes inactivated by antibiotic treatments. The minimum effective number of microbes sufficient to cause disease in humans is usually placed at $10^6$ or higher (Leggett, H. C., et al., 2012, 5.) Some diseases are localized, so that pathogens are relatively concentrated, such as urinary tract infections. Some antibiotics can concentrated at a local site, such as fosfomycin in the genitourinary tract. A single 3 gram dose can provide peak urinary concentrations for over 24 hours, sufficient to eliminate urinary tract disease by killing enough microbes. *Salmonella* infection is more widely spread, throughout the intestines. It has an ID50 (microbial quantity sufficient to cause disease in 50% of human population) of $10^9$ (Gama, J. A., et al., 2012, 6.) A seven day course of 500 to 1000 mg amoxicillin is considered standard, a total dose of 3.5 to 7 grams. (Monteagudo-Chu, 2017, 7.)

Of course antibiotics may not only inactivate disease causing pathogens, but also damage other microbes. At one extreme, a broad spectrum antibiotic may inactivate ten times more non-pathogenic microbes than pathogens. A narrow spectrum antibiotic may inactivate twice as many non-pathogens, or fewer.

Therefore antibiotic doses in the range of $10^1$ may inactivate about $10^{10}$ or $10^{11}$ microbes. Cattle may have up to $500^{12}$ microbes in their microbiome. A dose of 5 or 10 grams would presumably inactivate $10^{-3}$, or 0.02%, of the ruminant microbes. But STA doses for cattle are ≈100 mg per day, suggesting only $10^{-4}$, or 0.002% of microbes are inactivated. This is so exceedingly small it may be that continuous, daily STA doses have a much greater aggregate impact. But it is difficult to estimate the inactivation of more than $10^{-2}$, 1% or 2% of total rumenoreticulum microbes.

It has been the practice for some time now to place bolus-shaped objects in a ruminant's stomach to treat hardware disease, slowly deliver medicines, or to measure and broadcast conditions. U.S. Pat. No. 10,390,515 to Bancroft (P1) and 10,306,868 to Rettedal (P2) utilize hermetically sealed capsules positioned in an animal's digestive system that transmit environmental data.

U.S. Pat. No. 4,992,768 to Mozis (P3) and U.S. Pat. No. 7,289,011 to Tan (P4) are "cow magnets" that attract ingested metal objects and prevent hardware disease. Many dairy farmers place such magnets, around 4 inches in length and ½ inch height, in cattle reticulum, using a "bolus gun."

It is known that visible violet radiation of about 405 nanometers inactivates microbes, particularly gram negative pathogens. This is a Soret bandwidth, and activates microbe molecules called Porphyrins, that generate reactive oxygen species that disintegrate their own microbial cell walls. (Maclean et al., 2009, 8) found that Soret band light doses between 42 and 216 $J/cm^2$ reduced hospital microbes counts 2.6 to 4.7 $log_{10}$. This light is promoted by the U.S. Food and Drug Administration for use in blood transport, to prevent pathogen transmission without use of antibiotics (Atreya, C., et al., 2018, 9.) A 1 volt to 5 volt LED emitting Soret band light reduces microbe load by an order of magnitude within minutes, to a distance of 10 mm to 50 mm. Prior art does not teach the placement of Soret band light emitters inside a bolus-shaped object for placement in a ruminant rumenoreticulum, where it could reduce total microbe loads by amounts similar to STAs. It is also known that visible blue light radiation of about 420 nanometers eliminates methanogens in vitro. Use of this wavelength can reduce methane production.

SUMMARY OF THE INVENTION

The present invention provides an elongated capsule bolus that contains light sources. The interior of the capsule provides power sources sufficient to operate the light sources for a prolonged time period, of many months or years, a control system that manages electrical power, and thermal management. Some embodiments include sensors and/or signal emitters and receptors.

In its basic form the invention comprises a light emitting assembly adapted to be located in the rumenoreticulum of a ruminant animal. Single, double, or multiple vents or fins can be attached to the capsule exterior to position the device in the rumen. Or the device may be streamlined with a smooth exterior to ensure it lodges in the reticulum.

The capsule may emit light continuously, periodically, at predetermined times, according to sensor-detected local environmental conditions, or with instructions of an external operator. The capsule may communicate to a receiver external to the animal, by emitting a signal.

The present invention is generally administered by animal managers with a device they use for injecting boluses into cattle rumen, called a balling gun. If the capsule contains one or more sensors, these may communicate with the control system to activate light according to sensor-based data. A person external to the animal may activate the capsule light sources in response to signals they receive from the sensors.

A reduction in emitted light may be caused by fouling of light apertures. These may be cleaned with ultrasonic vibration, from a transducer vibrator embedded or enclosed near the emitting light. Cleansing of light apertures or areas may occur on a predetermined schedule, or because of user control, or may be triggered by a light detector. In this application, biocompatibility means the material will not promote cellular adhesion. The present invention provides for a biocompatible material in the form of a continuous, i.e., full-area, coating or shell to surround the capsule.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

Figure 1:
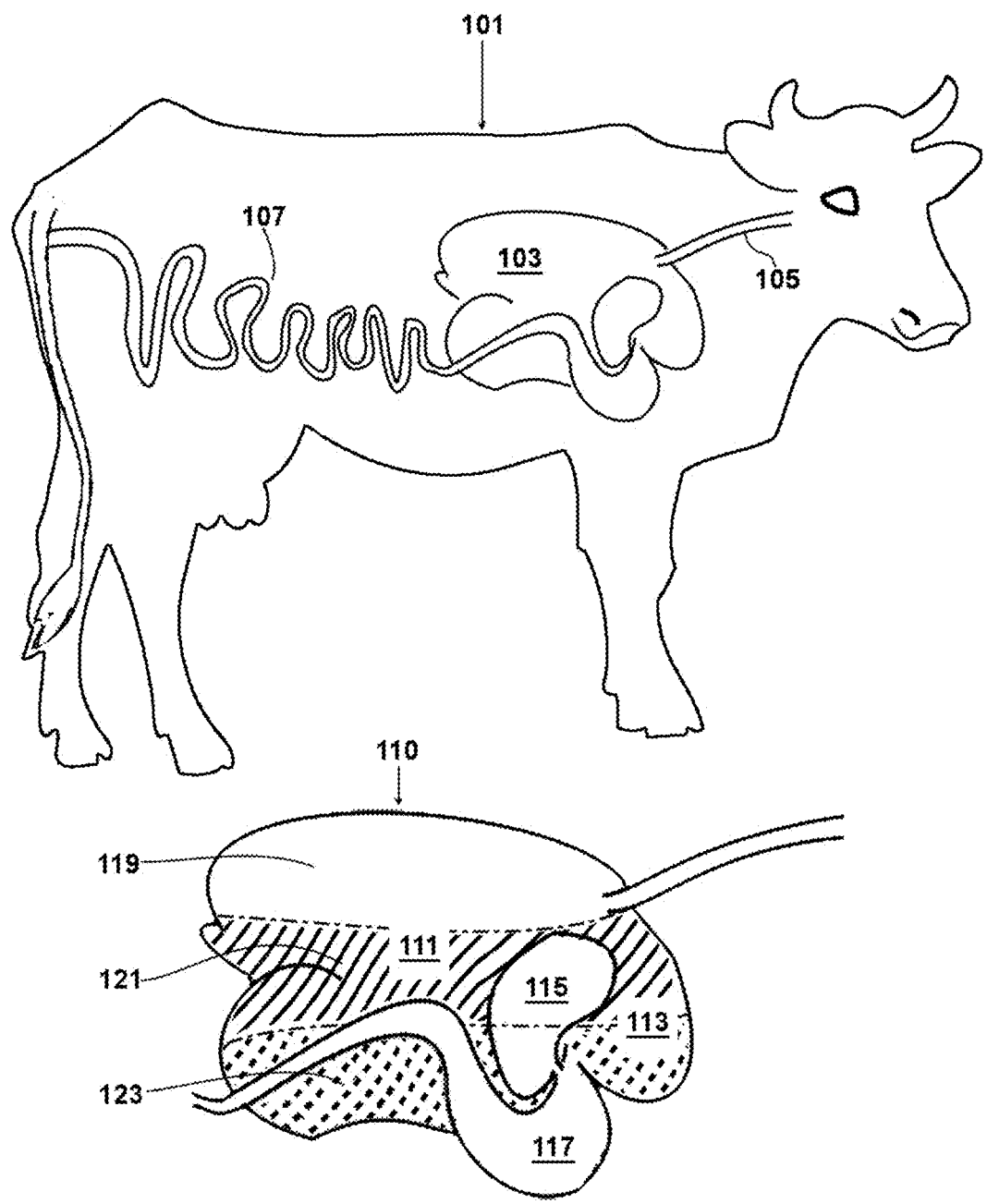
FIG. 1 is an image of a cow, illustrating the ruminant digestive system, and a schematic view of the four chambered stomach.

FIG. 1 is a side view of a cow 101 to which the invention may be administered. 105 illustrates the esophagus, 103 illustrates the ruminant stomach, and 107 the small and large intestine.

Referring to 110, a cow has four stomach compartments. The largest is rumen 111. The invention is administered orally through esophagus 105 and reaches rumen 111.

The other three stomach compartments are omasum 115, reticulum 113, and abomasum 117. Referring to 110, the interior of a cow stomach can be classified in three levels, upper level 119, middle level 121, and lower level 123. Upper level 119 is a gas layer filled with fermentation products such as methane and $CO^2$. Middle level 121, illustrated with lines, contains recently ingested materials and has thick viscosity. Lower level 123, illustrated with dots, is mostly liquid and contains many small particles.

In one embodiment, the weight of the invention and/or arm-like attachments on the invention cause it to be retained in rumen 111. If the embodiment weighs between 130 and 160 grams, it will settle into the liquid layer 121. In another embodiment, the weight and surface of the invention cause it to be retained in reticulum 113. This embodiment generally weighs less than 120 grams.

Figure 2:
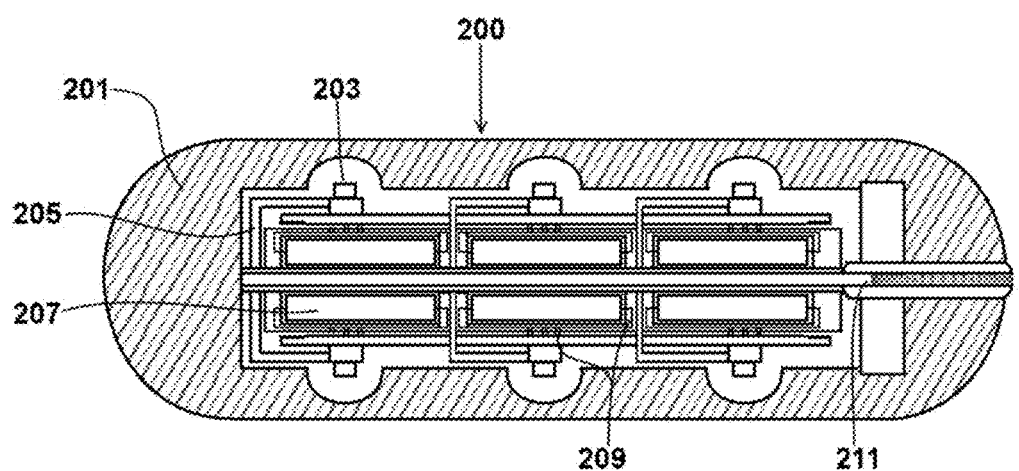
FIG. 2 depicts a schematic view of the current invention, illustrating inner components, and a perspective view of an embodiment.
Figure 2:
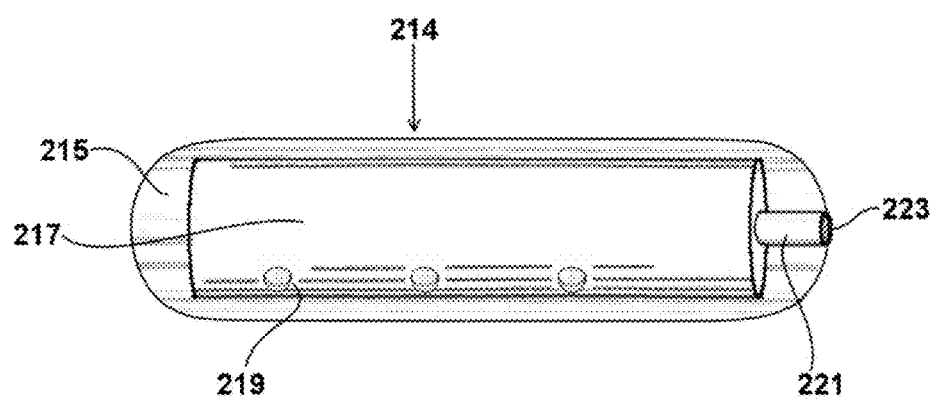

Referring to FIG. 2, illustration 200 is a cross-sectional view schematically illustrating the configuration of the light capsule in accordance with the first embodiment of the present invention. Light capsule 200 includes a transparent sealed housing 201, an array of light sources such as 203, a mechanism for evacuating heat 205 arranged between each light source 203 and heat sink 211, flat long-life batteries 207, and electrical connectors 209.

Referring to FIG. 2, illustration 214 is a perspective view showing an appearance of the light capsule in accordance with the first embodiment of the present invention. Light capsule 214 has a transparent housing 215 surrounding a cylinder 217 that contains each of the elements shown in illustration 200. Housing 215 is formed of transparent material sufficiently resistant to corrosion from the animal's digestive system. Cylinder body 217 has a metal body with apertures 219 capped by transparent material that is coupled to cylinder body 217. The main body of the heat sink (not shown) emerges at one end of cylinder body 217, where heat sink pipe 221 passes to an opening 223 in the transparent body 215.

Figure 3:
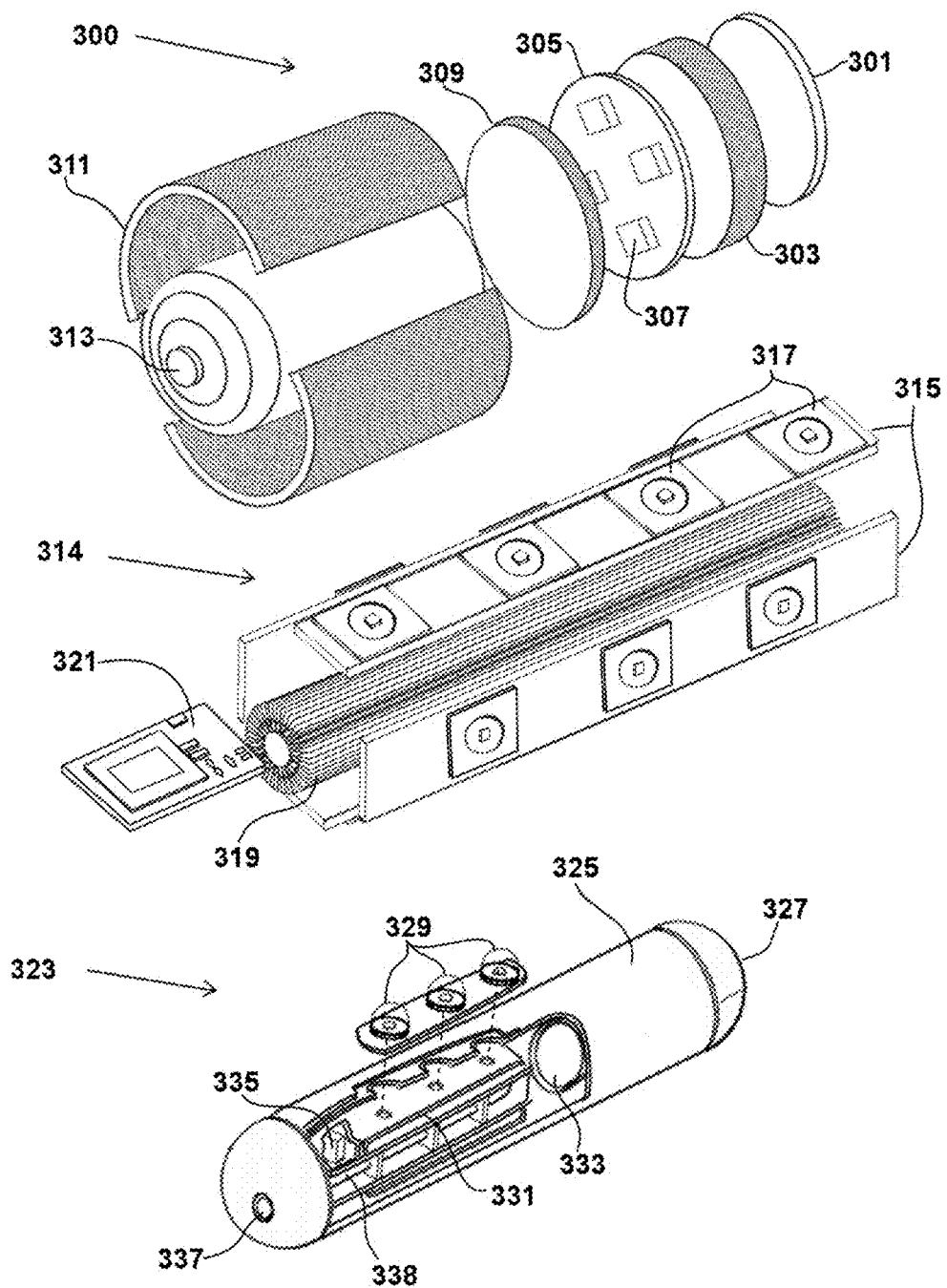
FIG. 3 is an exploded view of the internal components of the current invention, and a perspective view of an embodiment.

FIG. 3, illustrations 300 and 314, are exploded views of the light capsule, showing interior components. Referring to illustration 300, antenna 301 transmits and receives data through wireless communication to a receiver external to the animal. Antenna 301 is protected from electrical noise generated in the device by protecting portion 303. Wireless module 305 is electrically connected to antenna 301. Wireless module 305 includes processor, memory, and interface units 307, and includes amplifier capacity. Wireless module 305 is protected from electrical noise by protecting portion 309.

A battery 313 is held in a battery holder 311 that also serves to dampen electrical noise. The battery has a voltage sufficient to operate all light sources. Referring to illustration 314, light sources may be LEDs 317, arrayed on platforms 315. All platforms 315 are positioned around heat sink 319. Embodiments can vary in the number of light sources they contain. In general, the invention uses between six and twelve light sources. Wiring circuit board 321 is generally for controlling light sources. It outputs predetermined instructions to manage electrical circuits. It stores time data. In some embodiments, wiring circuit board 321 is capable of non-volatile memory storage that is rewritten by sensor input. When information is received from sensors it may be used to control light sources. Sensor data may be transmitted through wireless module 305 and antenna 301 to a receiver outside the animal.

Illustration 323 is a perspective view showing an appearance of light capsule that also displays some of the internal components in illustration 314 in cutaway. Referring to illustration 323, the light capsule has a housing 325 formed of metal, including a cap 327 attached to one end. At the other end of housing 325 is an opening 337 for evacuating heat from the heat sink 338. LEDs with transparent caps 329 fit onto platform 331. Wiring circuit board 335 is positioned near one end, and battery holder 333 at the other.

Figure 4:
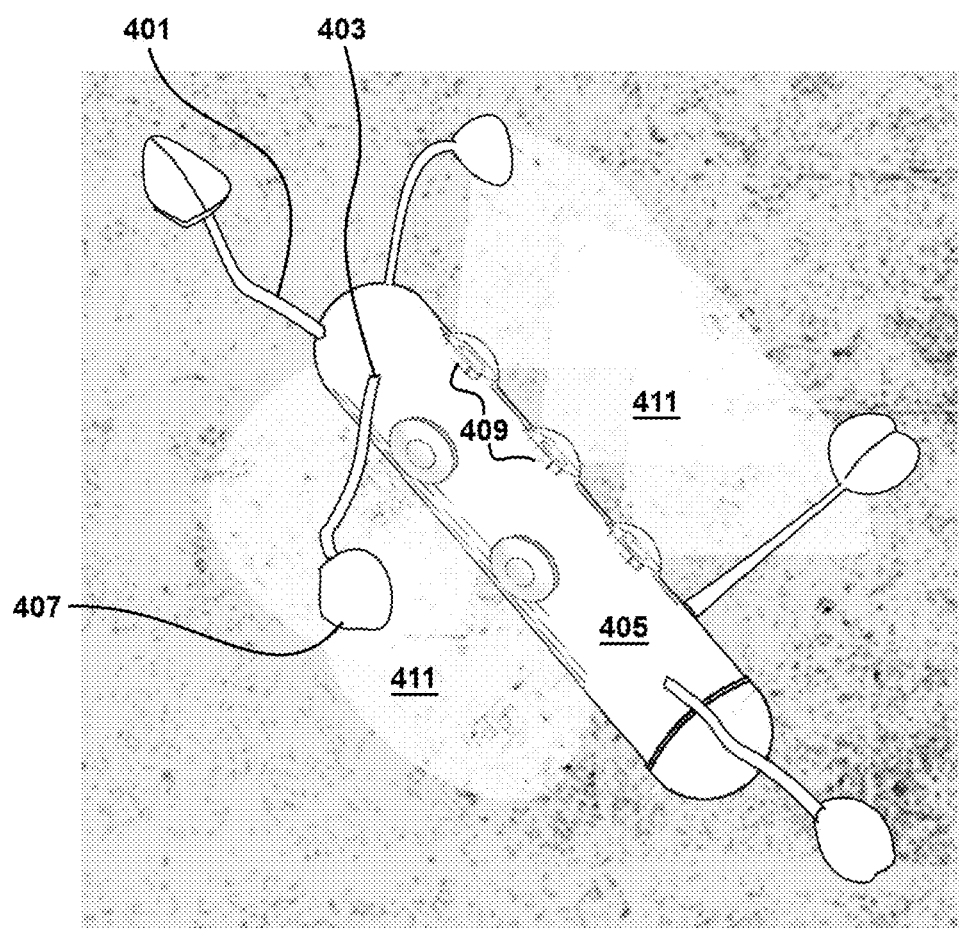
FIG. 4 illustrates the current invention in operation, suspended in a ruminant rumen.

FIG. 4 depicts another embodiment of the present invention, which includes arm-like appendages 401, each with a proximal and a distal end. The proximal end 403 is fixed into external surface 405 of the light capsule. The distal end 407 has bulbous sheaths that assist in preserving the light capsule's position in the rumen. The sheaths may contain sensors. Sensor data is transferred through the proximal end 403 of an appendage 401 inserted into the light capsule's body.

The light capsule is inserted into the stomach of a ruminant and reaches the rumen. This embodiment is configured so that is remains substantially near the top of the rumen liquid phase. This brings it in contact with concentrated microbial assemblages. The light capsule's light sources 409 radiate Soret band light to nearby areas 411, to diminish the live microbe load.

The light sources may remain active for predetermined periods, or be activated in response to sensor derived data, or because of human operator wireless input.

Figure 5:
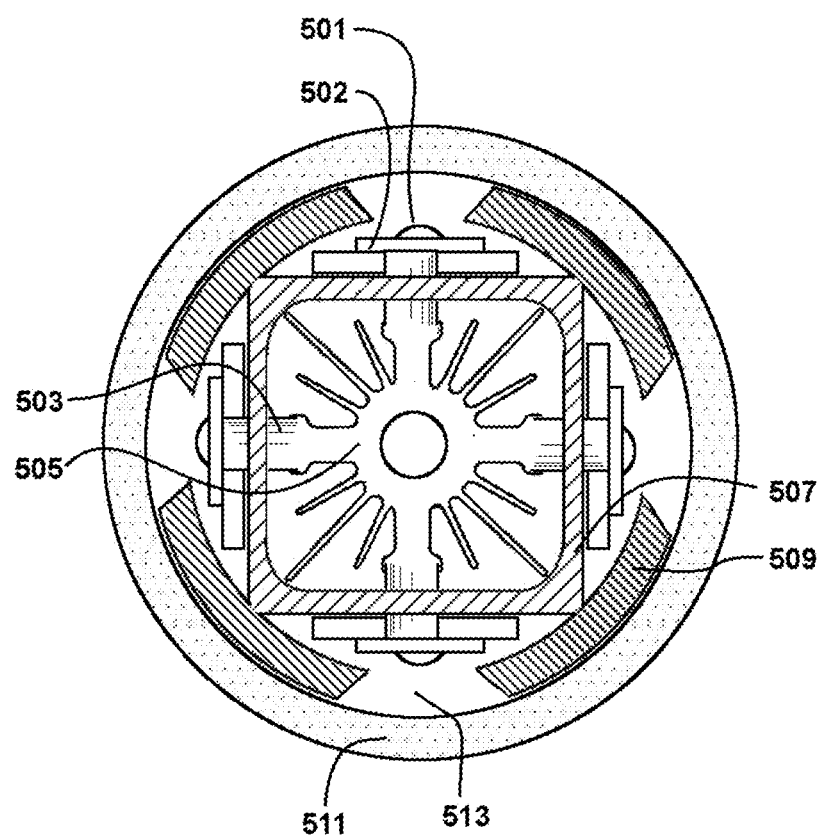
FIG. 5 depicts a schematic view of a cross-section of the current invention.

FIG. 5 is a cross-section schematic illustration of another embodiment. It uses a rectangular support structure 507 attached to a metal or other hard material cylinder 509. Support structure 507 fits tightly within cylinder 509. Each side of structure 507 supports a light plate 502 that is the base of a light source 501.

Any light source, included LEDs, generate heat that must be managed. Proper heat management preserves the potential lifespan of a light source, important for the long-term operation of the light capsule. Each light plate 502 is attached to heat sink 505 through heat pipe 503.

Light sources 501 emit radiation that escapes through opening 513. Cylinder 511 is transparent, permitting light to transit.

Figure 6:
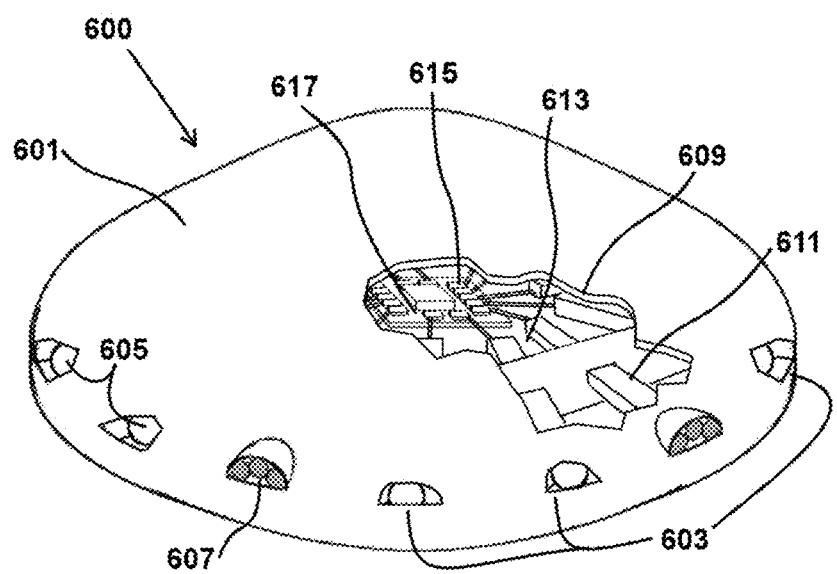
FIG. 6 illustrates a sensor and sensor configurations.
Figure 6:
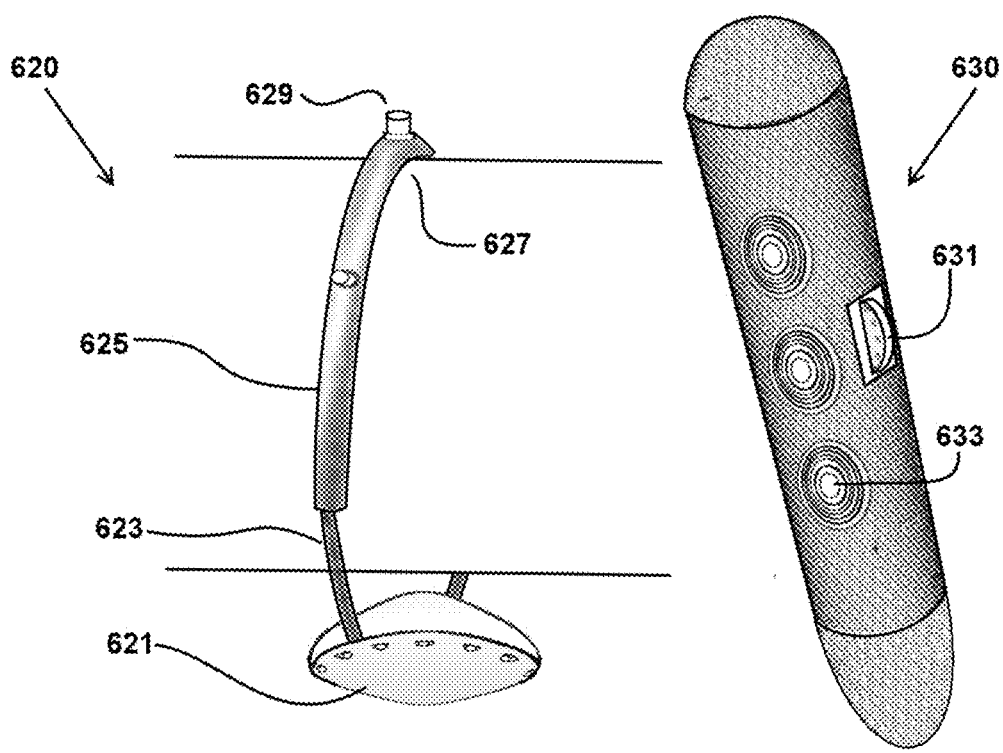

Sensor units can be configured in the bulbous ends of arm-like attachments, or attached to the main device. FIG. 6 illustration 600 depicts a pH, light and/or temperature sensor that includes a sensor body 601, with a plurality of apertures 603 that permit a ball-socket mechanism 605 to sample gastric fluid, and a plurality of apertures 607 that expose light detectors. Apertures 603 and 607 each contain an electrode. Referring to the cut-away 609, electrodes pass in conduits 611 into a protected interior 613 of the sensor unit, and connect to nodes 615 on circuit board 617.

Referring to illustration 620, a sensor 621 is directly electrically connected to ring 623 that slips into sheath 625, wherein an electrical connection to light capsule 627 occurs at position 629. Sensor 621 may have some degree of freedom of movement within sheath 625.

Referring to illustration 630 of an entire light capsule, sensor 631 is positioned as an appendage embedded in the capsule. Light sources 633 are positioned on a different axis than sensor 631.

Sensor data may be transmitted wirelessly to inform managers of stomach pH, a proxy for general microbial conditions. Managers can use this information to adjust light activation. Sensor data that detects light conditions may be used automatically to determine light activation, or initiate light lens cover cleaning.

Figure 7:
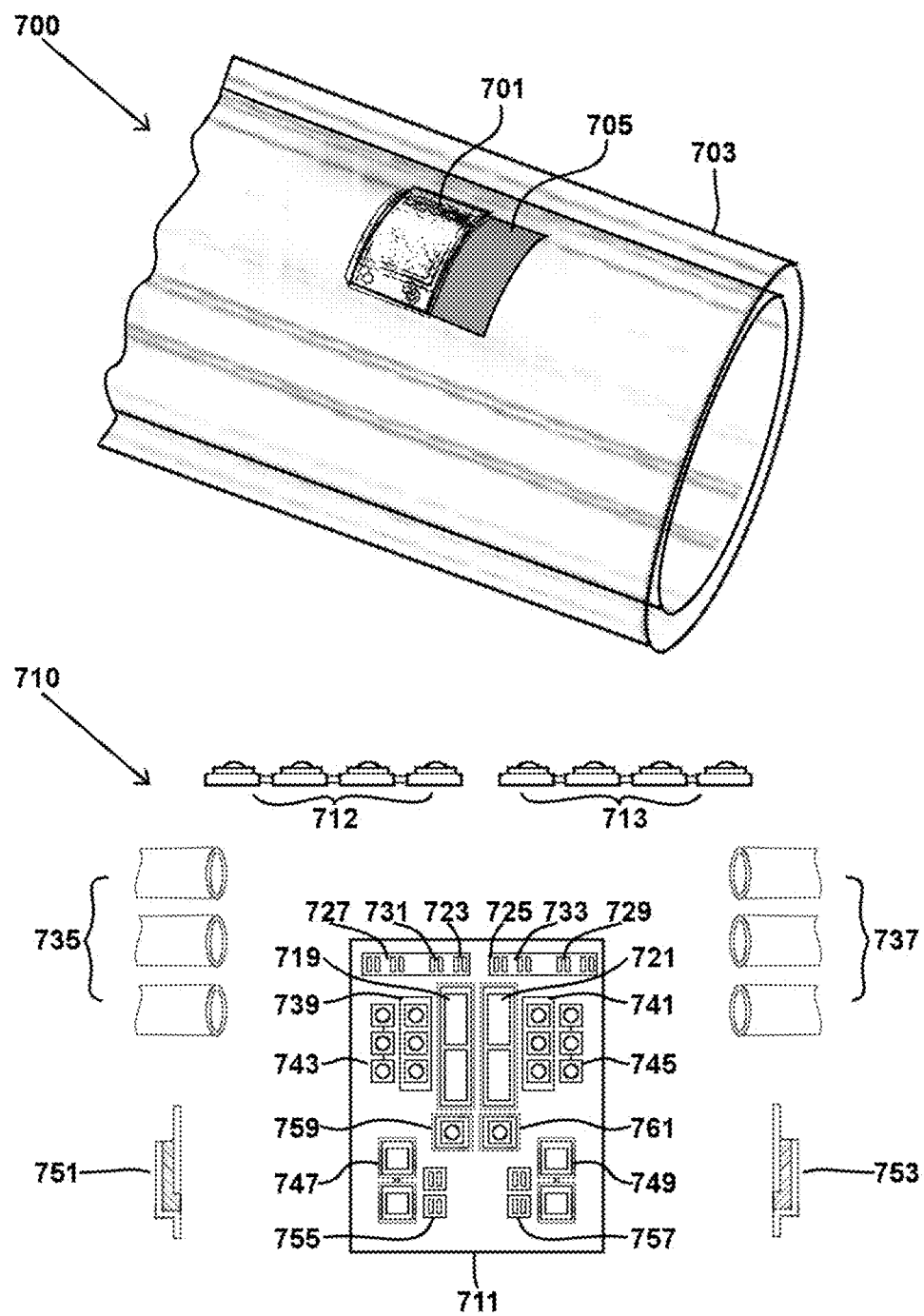
FIG. 7 illustrates an ultrasonic cleaning configuration for the current invention, and a schema of the wiring circuit board.

FIG. 7 illustration 700 depicts a piezoelectric element 701 which is embedded in the transparent housing polymer 703. Housing 703 surrounds the light capsule, not shown. Piezoelectric element 701, is a laminated sandwich of piezoelectric film by two electrodes. Vibrating film 705 is positioned directly below and next to piezoelectric element 701. 705 is embedded in housing 703. When a rectangular wave voltage of specific frequency is applied to piezoelectric element 701, it causes 705 to vibrate. This generates ultrasonic waves that move through housing polymer 703. These waves dislodge material attached to the surface housing 703, clearing it to permit better light transmission.

Referring now to illustration 710, wiring circuit board 711 powers light sources 712 and 713, connects sensors 735 and 737, and powers piezoelectric elements 751 and 753. Voltage converter modules 719 and 721 are configured to receive and convert input voltage into driving voltage. They may include a boost converter circuit, a buck converter circuit, and/or other suitable types of converter circuits. Module 719 enables series connection of LEDs 712 and module 721 enables series connection of LEDs 713. Module 719 powers switch transistor 723 and module 721 powers switch transistor 725 on a voltage regulated circuit. Transistors 723 and 725 may include a MOSFET, the drain of which is coupled to a cathode of the corresponding LED string. The output voltage from each LED is sampled continuously with sensing resistors 727 and 729 and compared to reference at comparators 731 and 733. Transistors 723 and 725 are adjusted automatically to maintain a constant output.

Each external sensor sends data through conduits 735 and 737 into the device, in this case data about pH that will be wirelessly transmitted through connectors 739 and 741, and light intensity data will be wirelessly transmitted through connectors 743 and 745 and/or light intensity data will be sent directly to voltage converter modules 747 and 749 which operate piezoelectric elements 751 and 753 through transistors 755 and 757. Piezoelectric elements 751 and 753 may also be operated through wireless direction, communicated through nodes 759 and 761.

Figure 8:
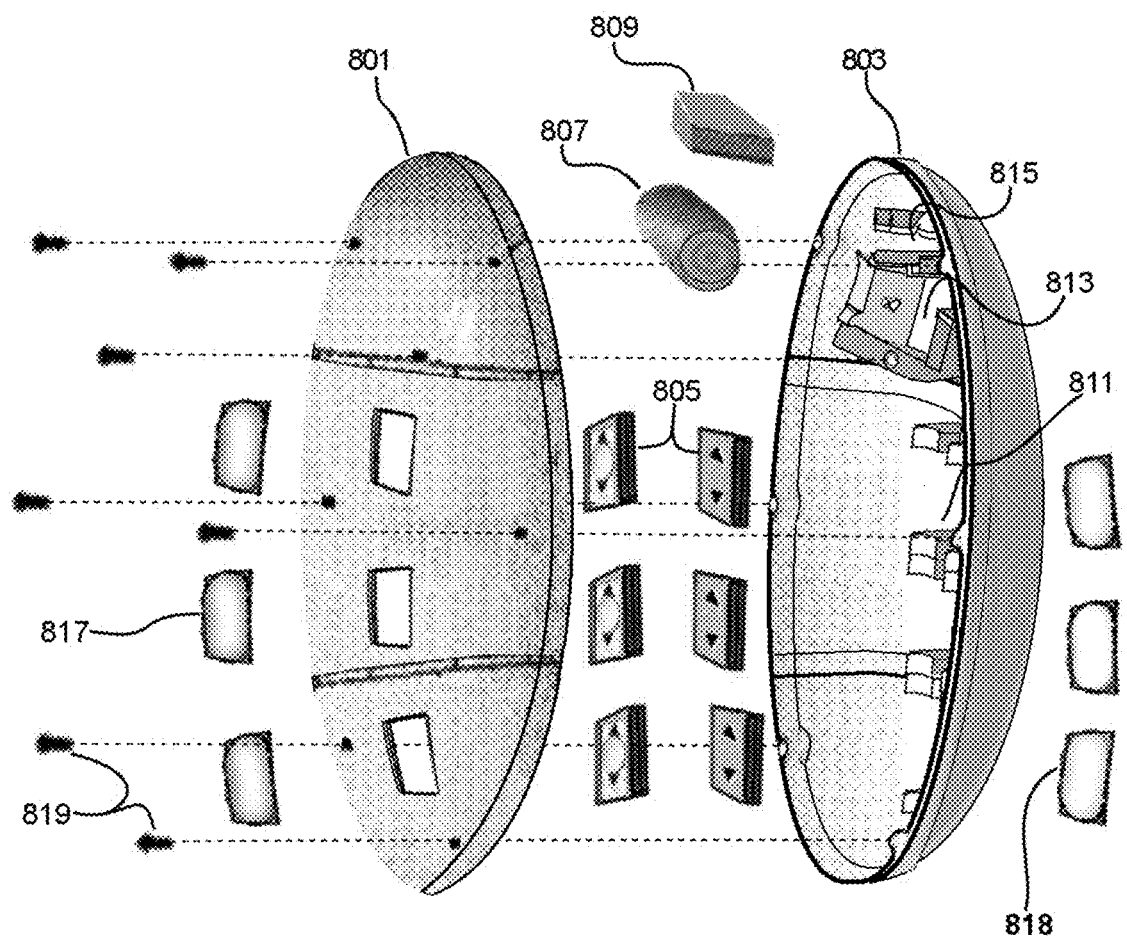
FIG. 8 is an exploded view of a plastic configuration of the current invention.

FIG. 8 is an exploded perspective drawing of a plastic capsule. Because of ruminant variability and the development of chemical resistant plastics, this embodiment uses a plastic material that is resistant to the rumenoreticulum environment. The embodiment illustrated in FIG. 8 is composed of a plastic casing including an upper housing 801 and lower housing 803 that defines a hollow compartment. The length dimension and width dimension of the plastic casing conforms to the dimensions necessary to position the device in a ruminant rumenoreticulum. The hollow compartment allows the light sources 805, power supply 807, and power control unit 809 to be fit into seating elements for lights 811, seating for power 813, and seating for control 815. Transparent aperture caps 817 and 818 cover the aperture through which light sources 805 radiate. Self-threading screws 819 close the plastic casing. There is sufficient empty space in the hollow compartment to permit thermal energy from light sources to dissipate without a heat sink. The thickness of plastic should be sufficient to prevent penetration from rough and sharp objects that may be present in the rumenoreticulum.

Figure 9:
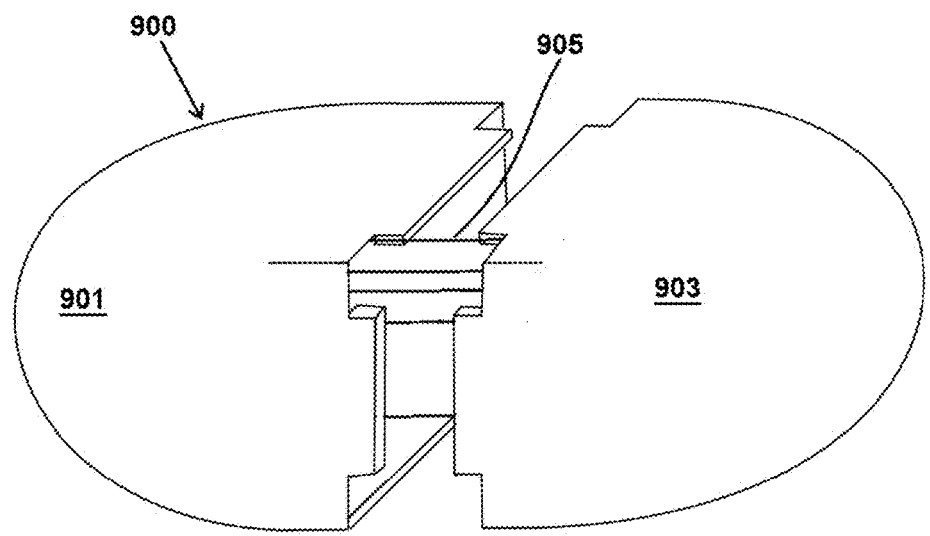
FIG. 9 illustrates a shape-shifting light capsule.
Figure 9:
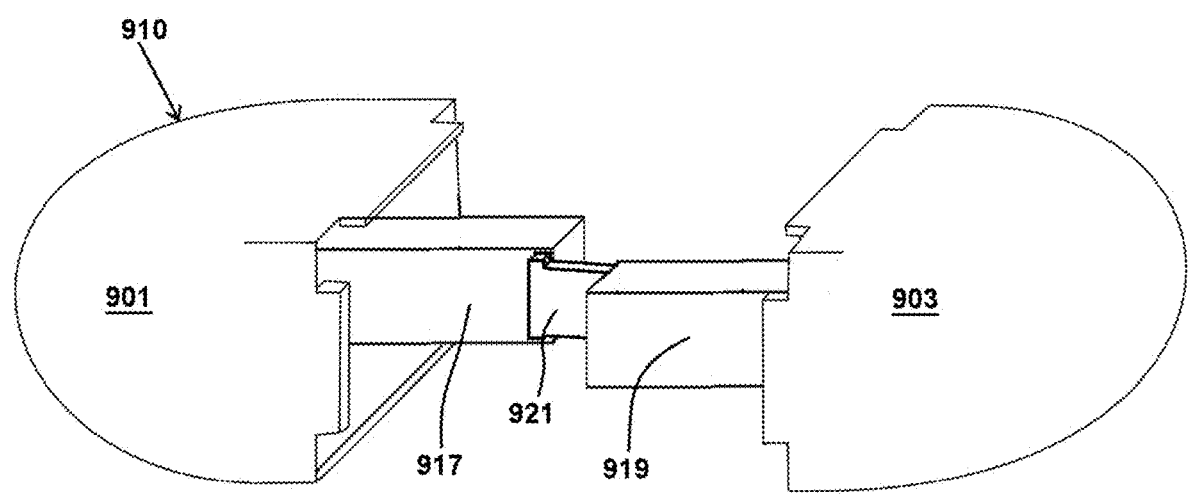

FIG. 9 illustration 900 depicts a perspective view of shape changing light capsule. First enclosure 901 and second enclosure 903 each separately contain one or a plurality of light sources. They may share or separately contain a power controller and power supply. They may also be configured with one or a plurality of sensors and an antenna to communicate wirelessly with users. First enclosure 901 and second enclosure 903 are connected by movable module 905, depicted in a closed, or shortened, configuration.

FIG. 9 illustration 910 depicts a perspective view of the shape changing light capsule with a first member 917 of the movable module and a second member 919 of the movable module shown in an extended, or lengthened, configuration. Axle 921 shifts position to extend or contract the two module members. At least one of the two module members contains at least one power source and at least one power controller. At least one of the two module members may also contain a sensor that detects biological data. At least one of the two module members may also contain a wireless communication capacity. The movable module extends and contracts in response to predetermined instructions, or in response to sensor data, or in response to user input wirelessly provided.

While the invention has been described in multiple embodiments, the words which have been used are words of description rather than limitation. Changes may be made within the purview of the claims without departing from the scope and spirit of the invention. For example, the cross-section of the light capsule was shown as circular, but may be of any shape. Each embodiment was shown as containing LEDs, but light sources of differing sizes and shapes may be used. Materials other than polymers may be used to form the external housing, or a housing may not be used, if the device is only a hard capsule. Likewise the cylinder may be made of any material resistant to corrosion from the digestive environment. The dimensions may be varied as appropriate to user needs and manufacturing specifications. While the use of arm-like appendages was disclosed, the actual shape of appendages is not important to the practice of the invention. Likewise, the heat sink may take many shapes, so long as its properties effectively manage the thermal energy generated during light source operation.

The invention claimed is:

1. A light capsule that is retained in a ruminant reticulorumen, comprising a luminaire bolus formed of:
   at least one a case made of a corrosion resistant material; and
   within the at least one case:
   at least one energy source; and
   at least one light source emitting a radiation having a peak wavelength between 400 nm and 700 nm; and
   the radiation emitted by the at least one light source passes through the case;
   a controller;
   the radiation inactivating microbes;
   the light capsule being configured for permanent retention and prolonged operation in the reticulorumen.

2. The light capsule of claim 1, further configured with a heat sink for thermal energy control.

3. The light capsule of claim 1, wherein a continuous biocompatible material envelopes the at least one case, having a strength sufficient to resist rupture.

4. The light capsule of claim 3, wherein an ultrasonic transducer is located inside or adjacent to the continuous biocompatible envelope, the ultrasonic transducer capable of being activated to clean the continuous biocompatible envelope surface.

5. The light capsule of claim 1, wherein a communication unit is positioned in the capsule, configured to receive through wireless communication information that operates the capsule.

6. The light capsule of claim 1, wherein the device has at least one sensor unit configured to measure at least one parameter of a biological state of the ruminant reticulorumen, with at least one measurement communicated to a data control unit.

7. The light capsule of claim 6, wherein the data control unit determines activation of the light sources.

8. The light capsule of claim 6, wherein the data control unit sends data to a communication unit in the capsule configured to a) transmit through wireless communication the control unit data, and b) receive through wireless communication information that operates the capsule.

9. The light capsule of claim 1, further comprising one or a plurality of flat, round, or wing shaped appendages attached to the capsule.

10. The light capsule of claim 1, wherein the device is configured to emit light with peak wavelength between 350 and 800 nanometers.

11. A method to inactivate a quantity of microbes within a reticulorumen of a ruminant animal comprising:
   a) positioning a capsule with sufficient size and density to be permanently retained into the reticulorumen;
   b) defining at least one interior space of the capsule with a corrosion resistant shell;
   c) including at least one light source in the at least one interior space;
   d) energizing the at least one light source with a prolonged operation energy source;
   e) controlling the at least one light source;
   f) emitting wavelengths between 400 nm and 700 nm into the reticulorumen,
   g) transmitting substantially all of the wavelengths through the corrosion resistant shell into an area of the reticulorumen.

12. The method according to claim 11, further providing at least one sensor for obtaining biological data of the reticulorumen, the at least one sensor having a data storage capability, and a user accessing the at least one sensor data utilizing a radio frequency communication device.

13. The method according to claim 11, wherein the device is introduced to the reticulorumen of the animal by discharging the device into the upper esophagus of the animal using a balling gun.

14. The method according to claim 11, wherein the device is configured to emit light with peak wavelength between 350 and 500 nanometers.

15. The method according to claim 11, wherein the device is configured to emit light with peak wavelength between 500 and 850 nanometers.

16. A light capsule that is retained in a ruminant reticulorumen, comprising a luminaire bolus having sufficient density to be permanently retained in a ruminant reticulorumen, formed of:
   two or more cases, at least one of the two or more cases containing at least one light source emitting radiation between 400 nm and 700 nm into the reticulorumen;
   at least one corrosion resistant shell defining at least one of the two or more cases;
   the radiation inactivating microbes;
      a movable module attached to at least one of the two or more cases;
      the movable module comprising at least one linear member and a movable axle to push apart or pull together the two or more cases;
   at least one energy source and at least one controller;
   the controller changing the external dimensions of the luminaire.

17. The light capsule of claim 16, further comprising the luminaire is configured with at least one sensor that measures biological data, and the controller responds to the at least one sensor data.

18. The light capsule of claim 16, further comprising the luminaire is configured with a communications system capable of wireless transmission and reception, permitting users to control the activity of the luminaire.

* * * * *